United States Patent
Johannesson et al.

(10) Patent No.: US 12,400,757 B2
(45) Date of Patent: Aug. 26, 2025

(54) MEDICAL DEVICE AND METHOD FOR REMOTE-CONTROL OF A MEDICAL DEVICE

(71) Applicant: Gambro Lundia AB

(72) Inventors: Camilla Johannesson, Lomma (SE); Mikael Lindhult, Lund (SE); Niklas Mebius, Bunkeflostrand (SE)

(73) Assignee: GAMBRO LUNDIA AB, Lund (SE)

( * ) Notice: Subject to any disclaimer, the term of this patent is extended or adjusted under 35 U.S.C. 154(b) by 74 days.

(21) Appl. No.: 17/605,848

(22) PCT Filed: Apr. 16, 2020

(86) PCT No.: PCT/EP2020/060643
§ 371 (c)(1),
(2) Date: Oct. 22, 2021

(87) PCT Pub. No.: WO2020/216664
PCT Pub. Date: Oct. 29, 2020

(65) Prior Publication Data
US 2022/0223277 A1    Jul. 14, 2022

(30) Foreign Application Priority Data
Apr. 24, 2019 (EP) .................................... 19170756

(51) Int. Cl.
*G16H 40/67* (2018.01)
*A61B 5/00* (2006.01)

(52) U.S. Cl.
CPC ........... *G16H 40/67* (2018.01); *A61B 5/0022* (2013.01)

(58) Field of Classification Search
CPC ............................. G16H 40/67; A61B 5/0022
See application file for complete search history.

(56) References Cited

U.S. PATENT DOCUMENTS

| | | | | |
|---|---|---|---|---|
| 8,907,909 B2 * | 12/2014 | Bello | ..................... | G16H 30/20 |
| | | | | 345/173 |
| 2005/0102167 A1 * | 5/2005 | Kapoor | .................. | G16H 40/20 |
| | | | | 705/3 |

(Continued)

FOREIGN PATENT DOCUMENTS

| KR | 20160010716 A | 1/2016 | | |
|---|---|---|---|---|
| WO | WO-2014111468 A1 * | 7/2014 | ............. | G06F 19/00 |

*Primary Examiner* — Sheetal R Paulson
(74) *Attorney, Agent, or Firm* — K&L Gates LLP

(57) ABSTRACT

The disclosure relates to the field of medical devices, and more specifically to techniques for remotely controlling medical devices. According to a first aspect, the disclosure relates to a method of operating a medical device to enable a remote system to remotely control the medical device, wherein the medical device comprises one or more actuators 17 arranged to control a medical procedure. The medical device 10 is controlled by a software system including one or more medical processes involved in the operation of the medical device during the medical procedure and a remote-control process. The method comprises handing over S6 ownership of control of the one or more actuators 17 from the one or more medical processes to the remote-control process, upon at least one first pre-determined criteria being fulfilled S5, and sending S7, by the remote-control process, in response to ownership of control of the one or more actuators being handed over S6, an activate confirmation, to the remote system and/or to a user interface of the medical device 10. The activate confirmation is indicating that remote-control of the one or more actuators is active.

20 Claims, 8 Drawing Sheets

(56) References Cited

U.S. PATENT DOCUMENTS

| | | | |
|---|---|---|---|
| 2006/0235549 A1* | 10/2006 | Hearn | G16H 40/67 |
| | | | 378/51 |
| 2010/0115279 A1 | 5/2010 | Frikart et al. | |
| 2013/0169432 A1* | 7/2013 | Ozgul | A61B 5/0022 |
| | | | 340/539.12 |
| 2017/0296056 A1* | 10/2017 | Hresko | A61B 5/0015 |
| 2017/0372600 A1* | 12/2017 | Palin | H04W 4/80 |
| 2018/0001010 A1 | 1/2018 | Blümler et al. | |
| 2022/0406452 A1* | 12/2022 | Shelton, IV | A61B 34/37 |

* cited by examiner

MEDICAL DEVICE AND METHOD FOR REMOTE-CONTROL OF A MEDICAL DEVICE

PRIORITY CLAIM

The present application is a National Phase of International Application No. PCT/EP2020/060643, filed Apr. 16, 2020, which claims priority to EP Application Serial No. 19170756.1, filed Apr. 24, 2019. The entire contents of each application are incorporated herein by reference and relied upon.

TECHNICAL FIELD

The disclosure relates to the field of medical devices, and more specifically to techniques for remotely controlling automated medical devices.

BACKGROUND

An automated medical device is a machine, whether used alone or in combination, intended by the manufacturer to be used for humans or animals for a medical purpose. Such a medical purpose may include diagnosis, prevention, monitoring, treatment or alleviation of a disease, injury, or handicap.

Automated medical devices are frequently used in the health care sector and are subject to strict regulatory frameworks to ensure that they are safe and efficient.

In general, an automated medical device is operated by a software system (e.g. installed on the medical device), which is a complex system that needs to be carefully designed to mitigate the risk of malfunctions that may have health implications. The software system typically comprises software configured to cause the medical device to perform a medical procedure, such as a medical treatment or medical diagnosis. In some situations, it may be desirable to control a medical device remotely, e.g. to perform tests or for service purposes.

However, uncontrolled remote access of medical devices may imply safety risk, e.g. for future medical procedures performed by the medical device. This risk may be handled in different ways. For example, "Design of a secure remote management module for a software-operated medical device", by Urban Burnik Štefan Dobravec and Marko Meža, 2017 proposes a multi-layer machine design solution that eliminates remote connectivity risks by strict separation of regular device functionalities from remote management service. More specifically, this document presents a modular system for remote update and management of software-operated medical devices. The modular system physically separates management and regular operation functionality by design, thus enabling remote operations only while in the maintenance start-up mode and completely preventing any possible risk during regular operation. This solution enables remote access to a limited number of functions, namely remote access to operational parameters of a device, remote configuration and management of a device and remote device software update. Furthermore, this solution also requires that the medical device is rebooted in order for the remote access to be activated. Thus, this remote-control only supports remote-control of certain functions and also requires a restart between the normal operation and remote-control. Hence, there is a need for more flexible ways of remotely controlling medical devices in a controlled manner.

SUMMARY

It is thus an object of the disclosure to avoid limitations of prior art associated with remotely controlling a medical device in a controlled way. In particular, it is an object to provide a way for a remote system to directly control actuators of the medical device, without a need to reboot the medical device in between. It is a further object to provide a way to enable switching between normal operation (i.e. default main system state) of a medical device and remote-control of actuators of the medical device, without affecting safety of the medical procedure.

According to a first aspect, the disclosure relates to a method of operating a medical device to enable a remote system to remotely control the medical device. The medical device comprises one or more actuators arranged to control a medical procedure. The medical device is controlled by a software system including one or more medical processes involved in the operation of the medical device during the medical procedure. The medical device also comprises a remote-control process. The remote-control process is separate from the one or more medical processes. Furthermore, the remote-control process is configured to manage remote-control of the medical device from the remote system. The method comprises receiving, by the remote-control process from a remote system, an activate-request requesting remote-control of the one or more actuators. The method further comprises handing over ownership of control of the one or more actuators from the one or more medical processes to the remote-control process, upon at least one first pre-determined criteria being fulfilled. The method further comprises sending, by the remote-control process an activate confirmation, to the remote system and/or to a user interface of the medical device. The activate confirmation is sent in response to ownership of control of the one or more actuators being handed over. The activate confirmation indicates that remote-control of the one or more actuators is active. Thereafter, the medical device will attend to remote requests from the remote system to control the one or more actuators. In this way the remote system may directly control the actuators of the medical device and is not limited to software applications in the medical device. Thus, the remote system (or an operator of the remote system) has full flexibility in terms of what operations are to be remotely performed.

However, remote-control is only activated when the one or more first pre-determined criteria is fulfilled, e.g. when it is considered safe. Hence, the safety of the medical procedure is not jeopardized. Furthermore, by handing over control of the actuators to a dedicated remote-control process when remote-control is activated, it is avoided that the remote system accidentally controls the actuators when it is not supposed to.

Thus, the proposed method makes it possible to remotely perform e.g. diagnostic and production test sequences on the medical device without risking safety of the medical procedure and without an intermediate reboot. More specifically, the proposed method makes it possible to perform e.g. diagnostic tests on a medical device in a medical environment (e.g. a hospital) from a remote service centre.

In some embodiments, the at least one first pre-determined criteria comprise that the medical procedure is idle, that the service of the medical device is idle, that control can be handed over without risking safety, and that the remote system is known and authorised. Hence, remote-control may only be activated under certain controlled circumstances.

In some embodiments, the one or more actuators are, at each individual point in time when the medical device is switched on, either owned by the one or more medical processes or by the remote-control process. Hence, it is avoided that the actuators are controlled from multiple sources and with potentially conflicting input.

In some embodiments, that the remote-control process and the one or more medical processes are being separated implies that they have separate memory spaces, different priorities, individual process states, and/or are communicating using inter process communication. Hence, an error in one of the processes may not propagate to the other process in the medical device.

In some embodiments, the method comprises setting the one or more actuators in a controlled state before handing over ownership of control of the one or more actuators from the one or more medical processes to the remote-control process. Hence, it is assured that the medical device is ready to be remotely controlled, before remote-control is activated.

In some embodiments, the method comprises receiving, from the remote system by the remote-control process, control data for controlling the one or more actuators and controlling, by the remote-control process, the one or more actuators based on the control data upon remote-control being active. Hence, the remote-control process will only act on such control data when remote-control is activated.

In some embodiments, the control data comprises one or more actuator set values to be used by the one or more actuators, data controlling an actuator to open and/or close a valve, and/or data controlling an actuator to adjust rotation speed of a device in the medical device. Thus, the actuators controlling the components of the medical device may be directly controlled based on the control data. In other words, a diversity of functionalities of the medical device may be remotely controlled.

In some embodiments, the method comprises receiving, by the remote-control process, a deactivate-request from a remote system. The deactivate-request requests the medical device to deactivate remote-control of the one or more actuators. The method further comprises setting, by the remote-control process, the one or more actuators in a controlled state and handing back ownership of control of one or more of the one or more actuators. The method further comprises sending, from the remote-control process to the remote system and in response to ownership being handed back, a release confirmation indicating that remote-control of the one or more actuators has been inactive. Thereby, the remote system can deactivate remote-control when not needed anymore.

In some embodiments, the medical device comprises a protective system configured to supervise the medical procedure and the method comprises deactivating the protective system upon the at least one first pre-determined criteria being fulfilled. Hence, the protective system is only active, while the medical device performs therapy. Thus, remote-control may be performed without having an active supervision process that otherwise might issue alarms etc.

In some embodiments, the protective system comprises a supervision process, being separate from the one or more medical processes, wherein the supervision process is configured to control the protective system using one or more auxiliary actuators and the method comprises handing over ownership of control of the one or more auxiliary actuators from the supervision process to a remote-control process of the protective system, upon second pre-determined criteria being fulfilled. In these embodiments, the activate confirmation is sent in response to the remote-control process of the protective system taking over ownership of control of the one or more auxiliary actuators from the supervision process. Hence, it is the main system that controls the remote-control state of the protective system. Thereby, it is avoided that the main system and the protective system are in different remote-control states (i.e. that one is "remote-control active" and the other "remote-control inactive").

In some embodiments, the second pre-determined criteria comprise that the medical procedure is idle, that the protective system is inactive or idle, that control can be handed over without risking safety, and/or that the remote system is known and authorised. Thus, the supervision process may not turn off its supervision due to remote-control, while the one or more medical processes are active and e.g. performs therapy, when service is ongoing or in other situations when it is considered inappropriate.

In some embodiments, ownership of control of the one or more actuators is handed over by giving the remote-control process ownership of writing to an interface and thereby enabling the remote-control process to change parameters controlling the one or more actuators. In other words, the ownership implies that all processes are aware of who is the owner at each point in time. Thus, the processes will only have permission to write to the interface when they are the owners of the control of the actuators.

In some embodiments, the one or more actuators are configured to control at least one of: a valve, a pump and a heater used while performing the medical procedure. Hence, the remote system may access hardware used when performing the medical procedure by controlling the actuators. Thereby, the remote system may perform tests or service of the medical device.

In some embodiments, the method comprises providing sensor data to the remote system enabling the remote system to monitor the operation of the medical device. The sensor data may also be used while performing tests or service of the medical device According to a second aspect, the disclosure relates to a corresponding medical device configured to perform a medical procedure. The medical device comprises one or more actuators, a communication interface, a set of processors and memory. The one or more actuators are arranged to control the medical procedure. The communication interface is configured to enable communication with a remote system. The memory is storing a software system for execution by the set of processors. The software system includes one or more medical processes involved in the operation of the medical device during the medical procedure and a remote-control process being separate from the one or more medical processes. The remote-control process is configured to manage remote-control of the medical device from the remote system. Furthermore, the software system, when executed by the set of processors, performs the method according to the first aspect.

According to a third aspect, the disclosure relates to computer-readable medium comprising a software system for operating a medical device to perform a medical procedure, the software system including one or more medical processes involved in the operation of the medical device during the medical procedure and a remote-control process being separate from the one or more medical processes, wherein the remote-control process is configured to manage remote-control of the medical device from the remote system, wherein the software system, when executed by a set of processors of the medical device, performs the method according to the first aspect.

DETAILED DESCRIPTION

This disclosure proposes a flexible way of giving a remote system access to control actuators of a medical device, which does not require that the medical device be restarted in a special mode. Instead, it is herein proposed to use a dedicated process to handle remote-control. This process is configured to receive requests from a remote system and to only attend to these requests when remote-control is activated. A specific activation procedure is used to activate remote-control. The activation procedure may verify that remote-control can be activated without risking safety for e.g. ongoing or future treatments. The medical device will only process requests to remotely control actuators of the medical device, when the remote-control functionality has first been successfully activated. In some embodiments, a deactivation procedure is used to bring the medical device into normal operation mode in a way that prevents the actions performed under remote-control from affecting future medical procedures. In this way, it is possible to, under controlled conditions, allow a remote system to directly control the actuators of the medical device.

For better understanding of the invention, some example medical devices will first be described. A medical device is an automated apparatus or machine which is configured to be operated, optionally in combination with one or more other medical devices, to perform a medical procedure in relation to a human or animal subject. As used herein, a medical procedure may involve one or more of diagnosis, prevention, monitoring, treatment or alleviation of a disease, an injury, or a handicap, or monitoring for detection thereof.

Figure 1A:
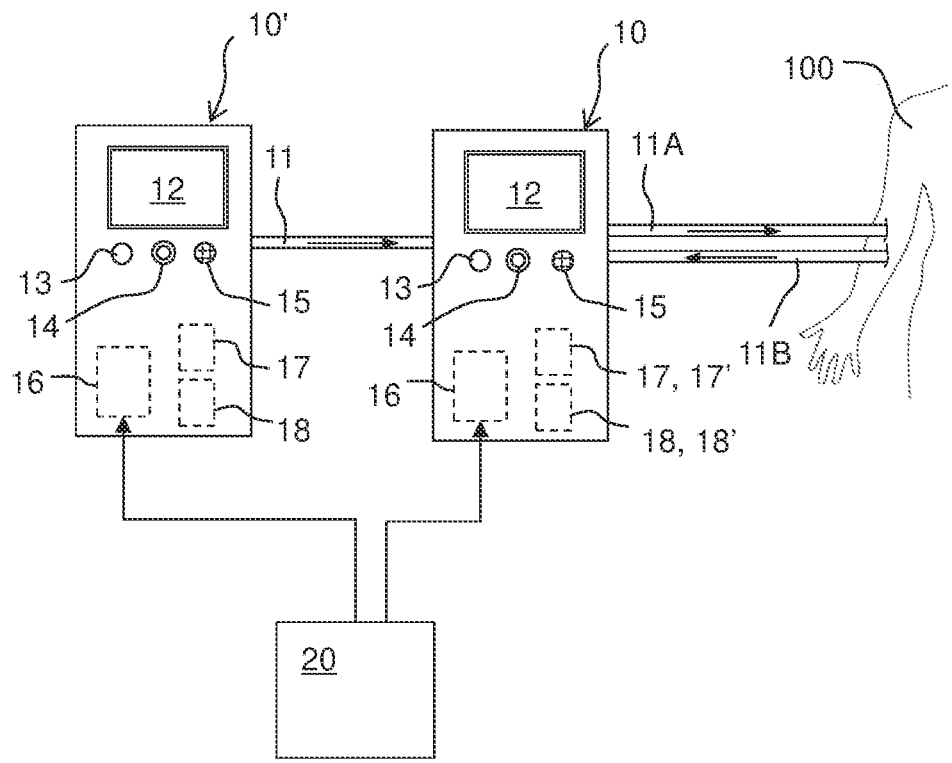
FIGS. 1a to c illustrate medical devices that may implement embodiments of the disclosed technique.

FIG. 1a illustrates two example medical devices 10, 10' which may be involved in a medical procedure of performing extracorporeal blood treatment, e.g. as part of renal replacement therapy, such as hemodialysis, hemodiafiltration, hemofiltration or isolated ultrafiltration. The medical device denoted 10 is a blood treatment apparatus, which comprises a blood withdrawal line 11A and a blood return line 11B for connection to the circulatory system of a subject 100, e.g. at a blood vessel access. As indicated by arrows, the medical device 10 is operable to withdraw blood from the subject 100, process the blood in a dialyzer (not shown) and return the processed blood to the subject 100 in a controlled manner, by means of e.g. a blood pump. In the dialyzer, blood is passed on one side of a semipermeable membrane and dialysis fluid is passed on the other side of the membrane. The membrane allows waste particles and water to move from the blood to the dialysis fluid, and desired particles to move from the dialysis fluid to the blood. The blood treatment apparatus 10 may also include a syringe driven by a syringe pump, where the syringe is used for heparin infusion or calcium infusion. The medical device denoted 10' is operable to prepare a fluid for use by the blood treatment apparatus 10 and comprises a fluid line 11 for supplying the fluid to the blood treatment apparatus 10. In one example, the medical device 10' is a water preparation apparatus and the fluid is purified water. For example, the water treatment apparatus 10' may filter incoming water by reverse osmosis, as known in the art.

In the illustrated examples, the medical device 10 comprises a display 12, control buttons 13 (one shown), an indicator lamp 14, a loudspeaker 15, a control system 16, one or more actuators 17 for controlled withdrawal, processing and return of the blood to the subject 100 via the blood withdrawal line 11A and a blood return line 11B, and one or more sensors 18 for providing sensor data indicative of the medical procedure performed by the blood treatment apparatus. The medical procedure may also include for example priming and function checks. The actuator(s) 17 and sensor(s) 18 may include internal components (as indicated by dashed lines) or external components of the medical device 10, or both.

The actuators 17 are, for example, configured to control a valve, a pump, and/or a heater while the medical procedure is performed. In other words, the actuators 17 are arranged to control the medical procedure. The actuator(s) 17 and sensor(s) 18 may also comprise auxiliary sensors 18' and auxiliary actuators 17' used to supervise the medical procedure. The auxiliary actuators 17' are for example configured to control an emergency valve or emergency brake to interrupt the medical procedure. To change e.g. a fluid flow rate the user typically inputs a set value for the fluid flow via for example a Graphical User Interface, GUI, generated on the display 12 or using the control buttons 13. This set value is then translated to one or more actuator set values, i.e. the values that controls the corresponding actuators. For example, a fluid flow rate of 300 ml/min (set value) is translated in pump rate in e.g. rpm or percent (actuator set value).

The control system 16 is configured to coordinate the operation of the actuator(s) 17 and the sensor(s) 18 to perform the intended medical procedure of the blood treatment apparatus, as well as to operate the display 12, the indicator lamp 14 and the loudspeaker 15 as needed in connection with the medical procedure, and to obtain user input via the control buttons 13. For example, the display 12 may be operated to present instructions to the user of the medical device 10, the indicator lamp 14 may be operated to indicate a medical device status, and loudspeaker 15 may be operated to generate an alarm signal, etc.

The medical device 10 is connected to a remote system 20 (only one illustrated but it may be a plurality). The remote system 20 is e.g. configured to remotely monitor and/or control the medical device. The remote system 20 will be further described in FIG. 2b.

The medical device 10' may have a similar set of components as the medical device 10, on the illustrated level of detail, and will not be described further. The medical device 10' is also connected to a remote system 20, in the same manner as the medical device 10. The medical devices 10, 10' may comprise more components than illustrated that will not be explained here for brevity.

Figure 1B:
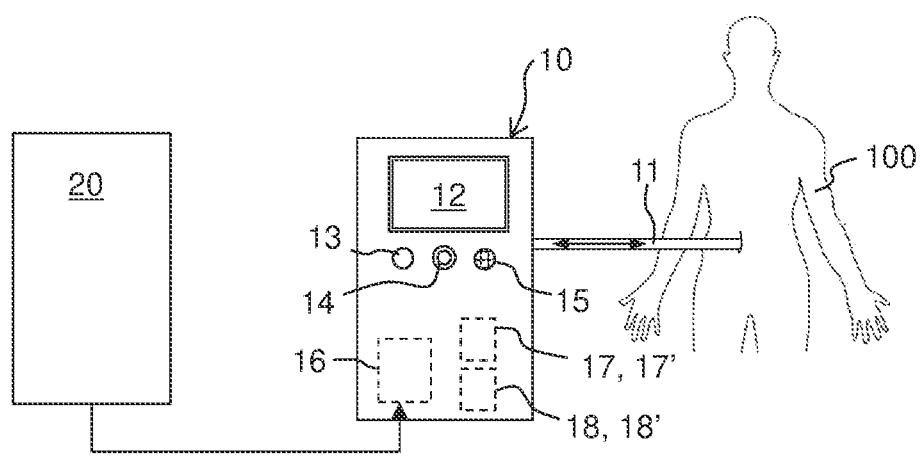

FIG. 1b illustrates another example medical device 10 which is operable to, in a controlled manner, deliver a dialysis fluid to the abdominal cavity of a subject 100 and subsequently remove the dialysis fluid therefrom, as indicated by a double-ended arrow. This medical procedure is commonly known as automated peritoneal dialysis, and the medical device 10 is often denoted a "PD cycler". The PD cycler comprises, for example, a pump for any of mixing, delivering and removing dialysis fluid. The medical device 10 in FIG. 1b may have a similar (but typically reduced) set of components compared to the medical device 10 in FIG. 1a, on the illustrated level of detail and may also be connected to a remote system 20. The medical device 10 in FIG. 1b may comprise more or less components than illustrated that will not be explained here for brevity. The medical device 10 may also be connected to another medical device 10' as illustrated in FIG. 1a, for obtaining purified water used for mixing dialysis fluid.

Figure 1C:
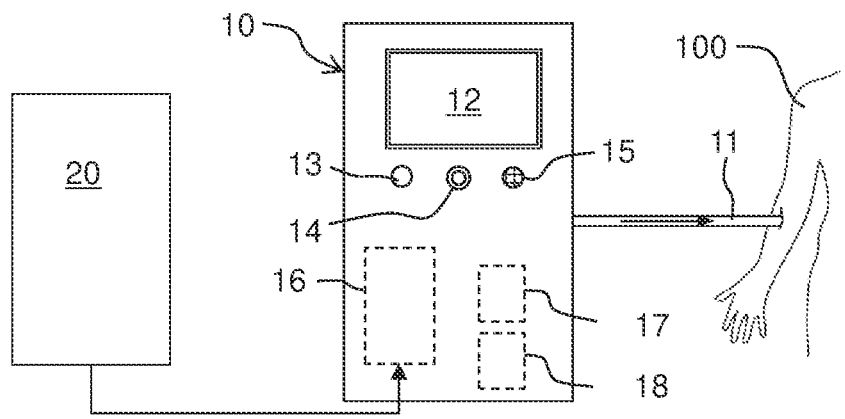

FIG. 1c illustrates a further example medical device 10, which is operable to deliver a medical fluid into the body of a subject 100, such as a human, in a controlled manner, as indicated by an arrow, e.g. into the circulatory system of the subject 100. The medical fluid may be any suitable liquid, including but not limited to medication and/or nutrients. This type of medical device 10 is commonly known as an "infusion pump". One or more actuators of the infusion pump is configured to control one or more pumps to pump medication and/or nutrients at a specified rate into the subject 100. Line occluders and/or valves are actuated for controlling the fluid flow during the pumping. The medical device 10 in FIG. 1c may have a similar (but typically reduced) set of components and may be connected to a remote system 20 as the medical device 10 in FIG. 1b, on the illustrated level of detail, and will not be described further. The medical device 10 in FIG. 1c may comprise more components than illustrated that will not be explained here for brevity.

Figure 2A:
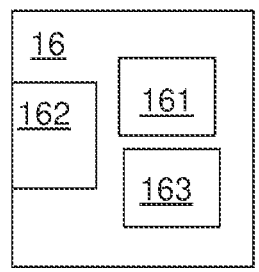
FIG. 2a illustrates a control system of the medical device of FIG. 1a to FIG. 1c in more detail.

FIG. 2a illustrates the control system 16 of any of the example medical devices of FIG. 1a-c in more detail, according to one example embodiment. The control system 16 comprises a processor 161, a communication interface 162 and memory 163. The processor 161 may be any commercially available processing device, such as a Central processing unit (CPU), Digital Signal Processor (DSP), a microprocessor, microcontroller, a Field-programmable gate array (FPGA), an Application-specific integrated circuit (ASIC), or any other electronic programmable logic device, or a combination thereof.

The communication interface 162 is configured to enable communication with the remote system 20 (FIG. 1a-c). The communication may be wireless and/or wired. Wired communication may be performed using a wired Ethernet connection, RS-232, RS-485 or UART. Wireless communication may be performed via any of Bluetooth™, WiFi™, Zigbee®, Z-Wave®, wireless Universal Serial Bus ("USB"), or infrared protocols, or via any other suitable wireless communication technology. The communication interface 162 is for example a Bluetooth™ chip, configured to be controlled by the processor 161. The communication between the remote system 20 and the medical device may be performed using any suitable communication protocol, such as Internet Protocol or a proprietary protocol.

The memory 163 may include non-volatile memory or volatile memory, or a combination thereof, including but not limited to Read-Only Memory (ROM), Programmable Read-Only Memory (PROM), Electrically Erasable Programmable Read-Only Memory (EEPROM), flash memory, removable memory, Random-access memory (RAM), Dynamic random-access memory (DRAM), Static RAM, cache memory, hard drive, storage medium, etc. The memory 163 stores a software system for execution by the processor 161. The software system is an integrated collection of software items organized to accomplish a specific function or set of functions, see ISO standard IEC 62304 regarding medical devices. The software system comprises application software and a software platform (typically including an operating system) that manages the software applications and acts as an intermediary between the applications and the hardware of the medical device. The software system may be accessed by remote systems 20 via the communication interface 162.

The software system is specified by one or more instructions stored in the memory 163 that are executable by the processor 161 to perform the operations described herein. The software system is configured to control the medical device 10 to perform e.g. the medical procedure. In other words, the software system includes one or more medical processes $P_{MED}$, involved in the operation of the medical device 10 during the medical procedure and a remote-control process $P_{RC}$ that is separate from the one or more medical processes $P_{MED}$. The concept of processes being separate from each other is further described in connection to FIGS. 4a-4c below. The remote-control process $P_{RC}$ is configured to manage remote-control of the medical device 10 from the remote system 20. The software system performs, when executed by the processor 161, the method of the first aspect (FIG. 4a-c), which will be described in detail below.

The processor 161 and memory 163 are "separate" in the sense that they are individually operable units, while they may or may not be located in any combination on a common substrate, e.g. in an integrated circuit. For simplicity, the control system 16 of FIG. 2a is illustrated as comprising only one processor 161, and memory 163. However, it should be appreciated that the medical device 10 may comprise a set of processors comprising one or more processors 161 and that the memory 163 may be implemented by one or several memory devices.

Figure 2B:
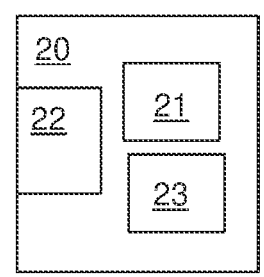
FIG. 2b illustrates a remote system configured to remotely control the medical device.

FIG. 2b illustrates an example remote system 20 in further detail. A remote system 20 is any system that is not an integrated part of the medical device, or more specifically of the software system executed by the set of processors 161 of the control system 16 of the medical device 10. The remote system 20 is e.g. a service or support system. The remote system may comprise one or more of a server, workstation laptop, computer etc. In practice it is possibly to perform any procedure remotely, even a medical procedure. The remote system 20 may be located on-site or off-site. In its simplest form, the remote system is a user device such as a tablet or personal computer, which has software configured to remotely control the medical device 10 installed thereon. The remote system 20 comprises a processor 21, a communication interface 22 and memory 23. The processor 21 may be any commercially available processing device, such as a CPU, DSP, a microprocessor, an FPGA, an ASIC, or any other electronic programmable logic device, or a combination thereof.

The communication interface 22 is configured to enable communication with the medical device 10. The communication may be wireless and/or wired. Wired communication may be performed using a wired Ethernet connection, RS-232, RS-485 or UART. Wireless communication may be performed via any of Bluetooth™, WiFi™, Zigbee®, Z-Wave®, wireless Universal Serial Bus ("USB"), or infrared protocols, or via any other suitable wireless communication technology. The communication interface 22 is for example a Bluetooth™ chip, configured to be controlled by the processor 21. The communication between the remote system 20 and the medical device 10 may be performed using any suitable communication protocol, such as Internet Protocol or a proprietary protocol.

The memory 23 may include non-volatile memory or volatile memory, or a combination thereof, including but not limited to ROM, PROM, EEPROM, flash memory, removable memory, RAM, DRAM, SRAM, cache memory, hard drive, storage medium, etc. The memory 23 store software for execution by the processor 21. The software is e.g. configured to control the medical device 10 to perform e.g. service, support.

For simplicity, the remote system 20 of FIG. 2b is illustrated as comprising only one processor 21, and memory 23. However, it should be appreciated that the remote system 20 may comprise several processors and that the memory 23 may be implemented by one or several memory devices.

The remote system 20 is configured to receive information e.g. sensor data provided by the sensors 18, from the medical device 10, via the communication interface 22. The remote system 20 may also send remote-control information to the medical device 10 e.g. to remotely control the actuators 17 in order to perform a service, tests (e.g. diagnostic tests or production tests) or other support procedure. For example, the remote-control information comprises one or more actuator set values. Then, the medical device 10 does not need to translate the remote-control information. The communication is typically implemented using messages communicated via the communication interface 22. The messages may be indicative of different commands (requests and responses) or they may carry data (e.g. actuator control data and/or sensor data).

The remote-control is e.g. performed by running a software application e.g. a diagnostic test or production test, in the remote system 20. Hence, in some embodiments the remote system 20 comprises a software application configured to generate the remote-control information that controls the actuators 17 of the medical device 10. Note that such software applications may be added based on needs, without any change of the medical device 10, which increases flexibility for diagnostics and support.

Alternatively, the remote system 20 may comprise a user interface where a user may remotely control individual actuators 17 of the medical device 10, when remote-control is activated.

The proposed technique will now be described with reference to FIG. 3 to FIG. 5.

Figure 3A:
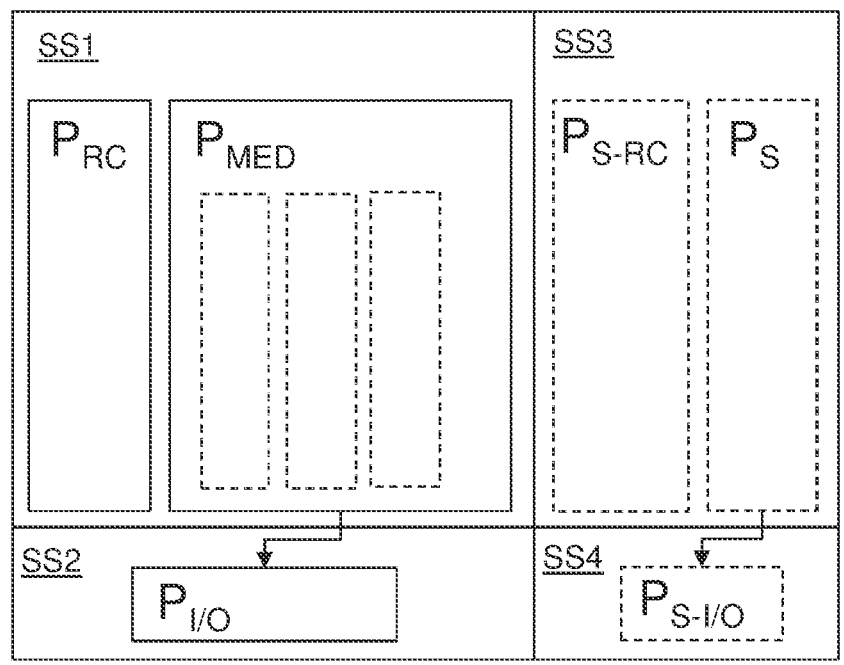
FIGS. 3a and 3b conceptually illustrate a software system for operating a medical device.
Figure 3B:
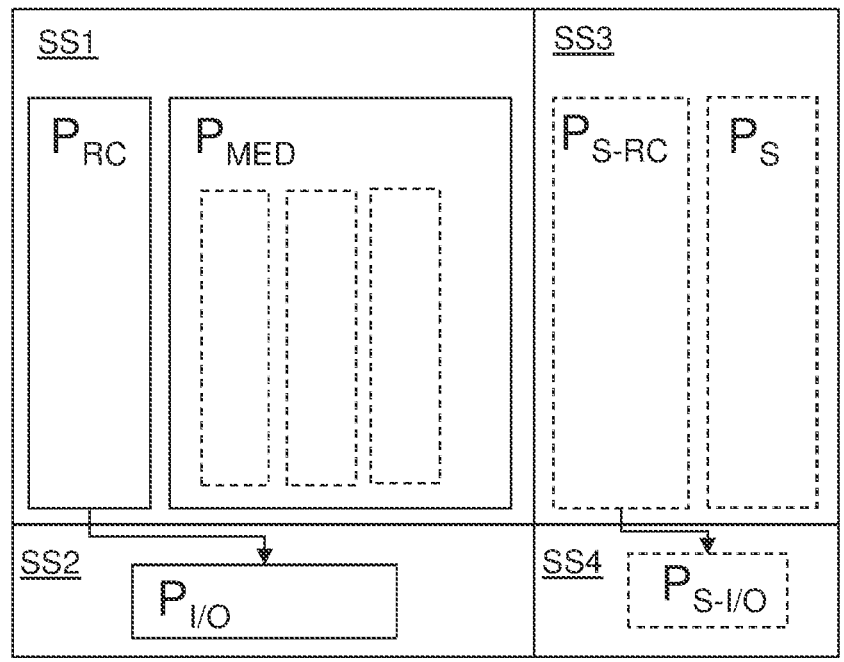

FIGS. 3a and 3b are block diagrams of an example software system configured to control the medical device 10, in accordance with a non-limiting example of the proposed technique. FIG. 3a illustrates the software system when operating the medical device 10 during normal operation, e.g. when performing the medical procedure. FIG. 3b illustrates the software system when remotely controlling operation of the medical device 10 e.g. for service or test purposes.

The illustrated software system comprises four subsystems SS, denoted SS1-SS4. The subsystems SS1-SS4 may be considered to be software modules of computer-executable instructions that may be independently developed and tested to provide specific functionality in relation to the operation of medical device when performing the medical procedure. Each respective subsystem comprises software processes (or threads) executed within the context of the respective subsystem. The software processes within a subsystem may thus be designed to perform a group of coordinated processes to provide the specific functionality of the subsystem. A process herein refers to a sequence of instructions that can be managed independently by a scheduler, which is typically a part of an operating system of the software system executed by the processor(s) 161 of the control system 16 of the medical device 10. The implementation of processes differs between operating systems. Different processes do not typically share resources such as memory spaces. The software processes are e.g. Linux processes or Green Hills Integrity processes. The operating system typically comprises a standard firewall, such as Netfilter, that monitors, and controls incoming and outgoing network traffic based on predetermined security rules.

The processes of the different subsystems communicate using inter-process communication (IPC), which refers to mechanisms of an operating system that allow the processes to manage shared data. For example, inter-process communication use clients and servers, where the client requests data and servers respond to client's requests. The inter process communication is up to implementation.

It is also conceivable that a subsystem includes one or more software processes that are not involved in the operation of the medical device. Further, a subsystem may include further software components, such as middleware and/or low-level software components that perform basic functions or services in the software system, such as a communication stack for managing communication with other subsystems, an error manager for managing technical errors, a notification manager for managing notifications, etc. One or more of the subsystems may be operated on top of one or more operating systems to make use of services provided by the operating system(s) in relation to hardware and software resources. Depending on implementation, the operating system(s) of the sub systems of the software system executed by the processor(s) 161 may, e.g., include a real-time operating system, an embedded operating system, a single-tasking operating system, or a multi-tasking operating system, or any combination thereof. It is also conceivable that one or more of the subsystems is configured to operate without an operating system and directly interface the hardware resources of the medical device.

Processes associated with the proposed technique will be described with reference to FIG. 3a. The first subsystem SS1 comprises one or more medical processes, $P_{MED}$, configured to control the medical procedure. Therefore, first subsystem SS1 is herein referred to as the main system of the medical device 10.

Many medical devices that perform a medical procedure that poses a health risk to a subject in case of operational failure in the main system that controls the medical procedure, or any of the hardware components used by such a main system, are required to include a protective system (also referred to as a supervision system) that operates in parallel and is independent of the main system. Whenever the protective system detects a potential operational failure (e.g. prediction of a state not matching the actual state), the medical device is switched to a safe operating state. Thus, in this example the third subsystem SS3 comprises a supervision process $P_S$ configured to supervise the operation of the medical procedure. The third subsystem SS3 is herein also referred to as the protective system of the medical device 10. In other words, the software system includes one or more medical processes, $P_{MED}$, involved in the operation of the medical device 10 during the medical procedure. In some embodiments, the medical device 10 also comprises a protective system configured to supervise the software system during the medical procedure. In some embodiments, the protective system comprises a supervision process, $P_S$, being separate from the one or more medical processes $P_{MED}$. However, note that the proposed technique may as well be implemented in medical devices that do not comprise a protective system SS3. Therefore, the processes of the protective system are illustrated with dashed lines in FIGS. 3a and 3b. If the protective system is omitted, the processes of corresponding SS3 and SS4 (and corresponding functionality) are simply omitted.

The subsystems SS2 and SS4 are I/O systems configured to communicate with different sets of actuators 17 and/or sensors 18 of the medical device 10 based on commands/ signals generated by the main system SS1 and the protective system SS3, respectively. To this end, each of the subsystems SS2, SS4 may comprise a software process for providing access to peripherals (e.g. actuators 17 and/or sensors 18 (FIG. 1a-c)) connected to the respective subsystem SS2, SS4. In FIGS. 3a and 3b these processes are denoted $P_{I/O}$ (short for I/O process) and $P_{S-I/O}$ (short for supervision I/O process). To achieve independence between the main system SS1 and the protective system SS3, the main system SS1 may be connected to a set of main sensors 18 and main actuators 17 (via the subsystem SS2) and the protective system SS3 may be connected to a separate set of auxiliary sensors 18' and auxiliary actuators 17' (via the subsystem SS4).

The subsystems SS1-SS4 are in some embodiments implemented on separate processors to achieve independence. Hence, during normal operation (i.e. when performing the medical procedure) the medical processes, $P_{MED}$ (i.e. the main system) and the supervision process $P_S$ (i.e. the protective system) are the owners of the actuators 17, which is illustrated by the arrow between the one or more medical processes $P_{MED}$ and the I/O process $P_{I/O}$ and the arrow between the one or more supervision processes $P_S$ and the I/O process $P_{S-I/O}$. That a process is designated as an owner on the actuators 17 means that no other process is allowed to control or write to the actuators, i.e. set the actuator values. A process is an owner, or process in control of, in the sense that it is the only process that is permitted to set the actuator values.

The main system SS1 also includes a remote-control process $P_{RC}$ that is separate from the one or more medical processes $P_{MED}$. The protective system SS3 may also (when present) comprise a remote-control process $P_{S-RC}$, which is separate from the supervision process $P_S$, which enables remote-control of the auxiliary actuators 17'.

The remote-control process $P_{RC}$ of main system SS1 is responsible for making it possible to remotely control the main system SS1 from a remote system 20, or more specifically to remotely control the actuators 17 of the medical device 10 from a remote system 20. The remote-control process $P_{RC}$ of the main system SS1 receives requests from the remote system 20 and, if remote-control is active, the medical device 10 will be controlled accordingly, as will be described in FIG. 4a-4c. Requests to control the auxiliary actuators 17' are forwarded to the remote-control process $P_{S-RC}$ of the protective system SS3. The remote-control process $P_{S-RC}$ of the protective system SS3 is responsible for making it possible to remotely control the protective system SS3 from a remote system 20, or more specifically to remotely control the auxiliary actuators 17' of the medical device 10 from a remote system 20. In other words, the remote-control processes $P_{RC}$, $P_{S-RC}$ are configured to manage remote-control of the medical device 10 from the remote system 20.

When remote-control is active, the one or more medical processes $P_{MED}$, (i.e. the main system) hand over the ownership of control of actuators 17 to the remote-control processes, $P_{RC}$. In the same way, the supervision process, $P_S$, (i.e. the protective system) hands over the ownership of control of auxiliary actuators 17' to the remote-control processes, $P_{S-RC}$ of the protective system.

The concept of ownership of controlling actuators will now be described with reference to FIG. 3b which illustrates the software system for operating a medical device 10 during remote-control, i.e. when remote-control is activated. In practice, the concept means that there is always one single owner (typically one or possibly a few processes) of the actuators. This owner has exclusive right or permission to controlling actuators. The ownership corresponds to a right (or permission), which is defined or implemented within the software system. This means that there is a "rule" within the software system that infers that only the "owner" of the actuators has permission to change it. The software system will be programmed in accordance with this rule, and also act accordingly. Hence, the ownership is not exposed externally to the software system. The ownership assists the software system in keeping control of the actuator settings. The ownership may be implemented using e.g. a state, variable or parameter that defines which process is in control of the actuator. The state, variable or parameter is then checked before controlling the actuators. The ownership is handed over (i.e. changed) by a handshake between the processes, as will be further described in FIG. 4a.

Controlling the actuators 17 (and auxiliary actuators 17' if present) from a remote system 20 means that the remote system 20 takes over control of the actuators 17 of the medical device 10 (FIG. 1a-c). In this situation, the one or more medical processes, $P_{MED}$, are in an idle state and do not control any actuators 17 as long as remote-control is active. The supervision process $P_S$ (if present) is also in an idle state and do not control any auxiliary actuators 17' as long as remote-control is active. Instead, the remote-control process $P_{RC}$ of the main system SS1 and the remote-control process $P_{S-RC}$ of the protective system SS3 are the owners of the actuator control. This is illustrated in FIG. 3b by the arrow between the remote-control process $P_{RC}$ of main system SS1 and the I/O process $P_{I/O}$ and the arrow between the remote-control process $P_{S-RC}$ of protective system SS3 and the supervision I/O process $P_{S-I/O}$.

Hence, the software system continually tracks and manages which process (or processes) is the owner of (i.e. is in control of) the actuators 17, i.e. which process, or processes, are allowed to set the actuator values. This means that, when the medical device 10 is switched on, the one or more actuators 17 are, at each individual point in time, either owned by the one or more medical processes $P_{MED}$ or by the remote-control process $P_{RC}$. Thus, if the remote system 20 tries to control the actuators, when the remote-control process $P_{RC}$ is not the owner of writing to the actuators 17, then the request will be neglected. In this way conflicts are avoided, as the actuators are always controlled by one single process and while the switching of the actuator control is done in a controlled manner.

In other words, when remote-control is activated, the medical processes, $P_{MED}$, and the supervision process $P_S$ hand over the ownership of control of actuators to remote-control process $P_{RC}$ of the main system and $P_{S-RC}$ of the protective system respectively. When remote-control is inactive, the ownership is returned to medical processes, $P_{MED}$, and the supervision process $P_S$.

Figure 4A:
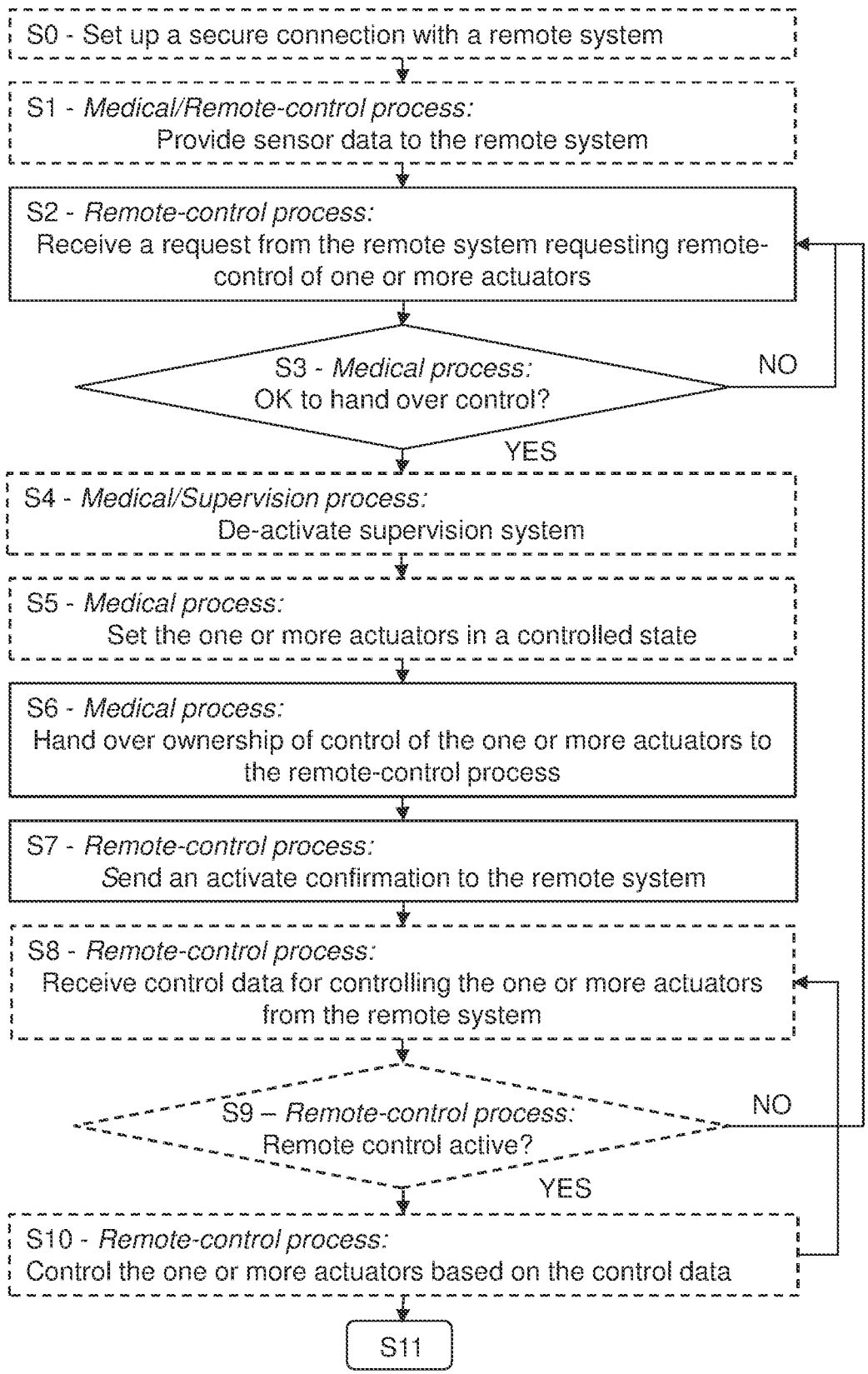
FIGS. 4a-4c are flow charts of methods for operating a medical device to enable a remote system to remotely control the medical device.
Figure 4B:
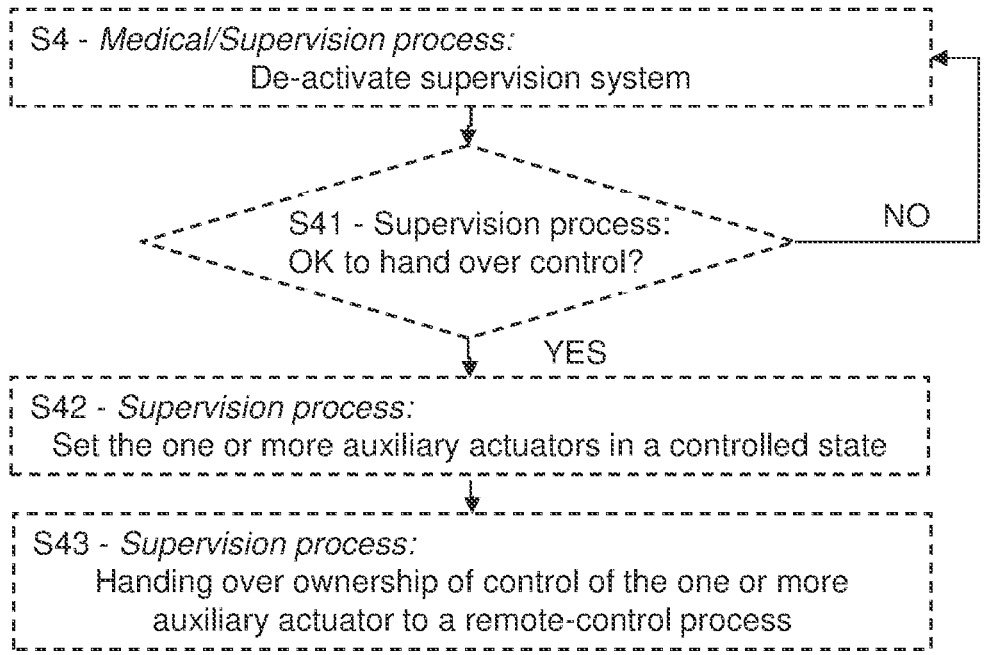
Figure 4C:
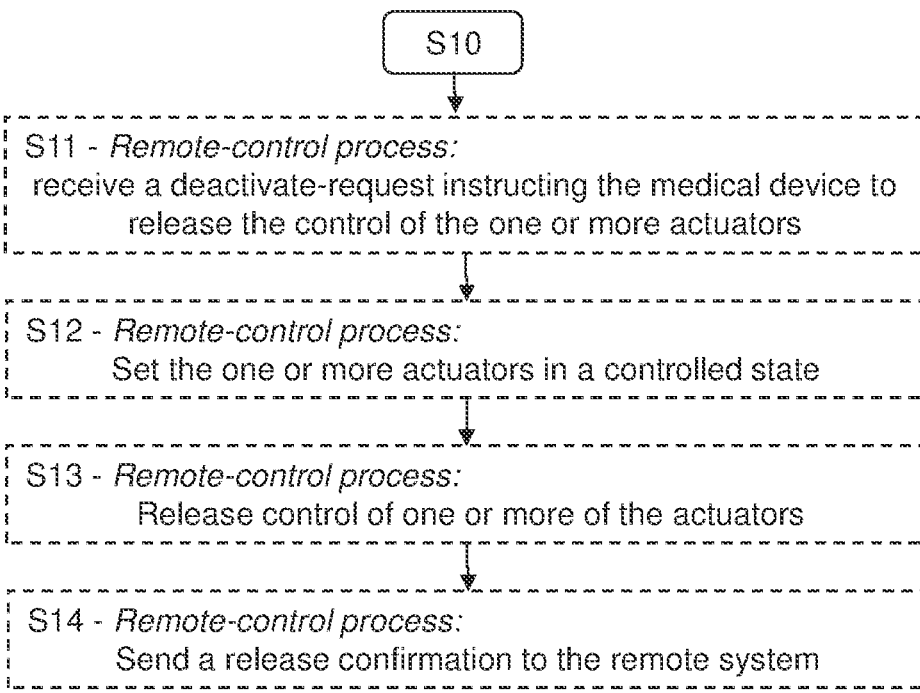

The proposed technique will now be described in further detail with reference to the flow charts of FIGS. 4a to 4c. FIGS. 4a to 4c illustrate an example method of operating a medical device 10, such as the medical device 10 of FIG. 1a-1c, to enable a remote system 20 to remotely control the medical device 10. The method is e.g. performed in a medical device 10 located in a medical care environment, such as a hospital, where the medical device 10 is used to e.g. treat patients. The method may also be performed in a medical device 10 at a patient's home. The method makes it possible to let a remote system located outside the medical care environment (and an operator of such a system) access the machine between the treatments e.g. to diagnose the medical device 10.

As described above, the medical device 10 is controlled by a software system including one or more medical processes $P_{MED}$ involved in the operation of the medical device 10 during the medical procedure and a remote-control process $P_{RC}$, being separate from the one or more medical processes $P_{MED}$. That the remote-control process $P_{RC}$ and the one or more medical processes $P_{MED}$ are being separated means for example that they have separate memory spaces, different priorities, individual process states or modes and/or are communicating using inter-process communication. In some embodiments, the medical device 10 comprises a protective system SS3 configured to supervise the medical procedure. However, the method may also be implemented in a medical device 10 without a protective system SS3. In this scenario the procedure is similar, but the signalling with the protective system SS3 is absent.

The method is typically implemented as a computer program comprising instructions which, when the program is executed by a set of processors, cause the computer to carry out the method. According to some embodiments the computer program is stored in a computer-readable medium that comprises instructions which, when executed by a set of processors, cause the computer to carry out the method.

The method may be performed anytime when the medical device 10 is switched on. A prerequisite for being able to perform the method is typically that the communication functionality used for "remote-control", e.g. the communication interface 162, is enabled. Also, the main system SS1 may need to be configured to receive (e.g. subscribe to) "activate/deactivate remote-control" notifications.

The initiation of remote-control and remote-control of actuators 17 will now be described with reference to FIG. 4a. To enable the remote-control to be activated, the remote system 20 first has to be connected to the medical device 10, such that the remote system 20 can communicate with the medical device 10. Thus, secure connection for exchanging information has to be established between the remote system 20 and the medical device 20, e.g. using the communication interface 162. The connection is, for example, an encrypted wireless or wired link established using commonly known techniques. In other words, in some embodiments, the method comprises setting up S0 a secure connection with a remote system 20.

When a connection is established between the medical device 10 and the remote system 20, the medical device 10 may continuously send information e.g. sensor data obtained by the sensors 18 to the remote system 20. More specifically, the remote-control process $P_{RC}$ can interface the sensors 18 via I/O systems configured to communicate with different sets of actuators 17 and/or sensors 18 of the medical device 10, as explained in FIG. 3a-3c. The sensor data may indicate pressures, rotation speeds, temperatures etc. measured in the medical device 10 by the sensors 18. The remote system 20 may request different types of sensor data e.g. log data. The remote system 20 may use the obtained sensor data to monitor the operation of the medical device 10. In other words, in some embodiments the method comprises providing S1 sensor data to the remote system enabling the remote system 20 to monitor the operation of the medical device 10.

When the remote system 20 wants to take over control of the medical device 10, an activate-request is sent from the remote system 20 to the medical device 10. The activate-request is a message that includes information that informs the medical device 10 that the remote system wants to take over control of one of more actuators 17 of the medical device. The activate-request is e.g. generated by a service or support program in the remote system 20. The activate-request is received by the communication interface 162. The medical device 10 may also comprise software (not shown) that checks that the activate-request is valid, before it is forwarded to the remote-control process $P_{RC}$. For example, it is checked that the remote system 20 is known and authorized to perform remote-control of the medical device 10. The activate-request is then received by the remote-control process $P_{RC}$, as this is the process handling communication with the remote system 20. In other words, the method comprises receiving S2, by the remote-control process $P_{RC}$ from a remote system 20, an activate-request requesting remote-control of the one or more actuators 17.

However, the medical device 10 will only accept to be remotely controlled if at least one first pre-determined criteria is fulfilled. The at least one first pre-determined criteria comprises for example that the medical procedure is idle (i.e. no therapy is ongoing), as it would typically not be safe to activate remote-control in the middle of a medical procedure. This can be detected by checking the mode or state of a software process that handles the medical procedure. For example, all previously initiated treatments (e.g. tasks) have to be finalised or terminated. The at least one first pre-determined criteria may also comprise that the service of the medical device is idle (i.e. no service is ongoing), as it is typically desirable not to interrupt a service that has been started. This can easily be detected by checking the mode or state of a software process that handles service of the medical device. For example, all previously initiated services (e.g. tasks) have to be finalised or terminated.

In some embodiments, the at least one first pre-determined criteria comprise that control can be handed over without risking safety. This indicates that remote-control is only activated if it is considered safe. Hence, actions are taken to avoid that the remote-control would not cause an uncontrolled pressure increase, flow of fluid etc. Another criterion that may be checked is that the remote system 20 is known and authorised.

If the at least one first pre-determined criterion is fulfilled, activation of remote-control will be initiated. If the medical device 10 comprises a protective system SS3 configured to supervise the medical procedure, then the protective system SS3 is typically inactive during remote-control. In some embodiments an alternative protective system configured to supervise the remote control is activated instead, as will be further described below. Thus, in these embodiments, the method comprises deactivating S4 the protective system SS3 upon the at least one first pre-determined criteria being S3 fulfilled.

It may also be desirable to always make sure that the medical device 10 is in a neutral or at least known state when remote-control is activated. Hence, valves, pumps etc. should typically be in a neutral state where there is no risk for leakage or other damage. For example, all pumps are stopped before remote-control is activated as it may be considered inappropriate to hand over control of the medical device 10 when a pump is rotating. Hence, in some embodiments, the method further comprises setting S5 the one or more actuators 17 in a controlled state before handing over ownership of control of the one or more actuators 17 from the one or more medical processes $P_{MED}$ to the remote-control process $P_{RC}$. The controlled state is e.g. a default state defined by the manufacturer.

When the medical device 10 is ready to be remotely controlled, the control of the actuators will be handed over to the remote-control process $P_{RC}$. This means that the remote-control process $P_{RC}$ may receive commands from the remote system 20 and control the actuators 17 accordingly. In practice this means e.g. that the one or more medical processes $P_{MED}$ informs the remote-control process $P_{RC}$ that remote-control is active. Thereby, the one or more medical processes $P_{MED}$ have validated the activate-request. Furthermore, the one or more medical processes $P_{MED}$ and the remote-control process $P_{RC}$ updates its status to "remote-control is active". Thereby, the remote-control process is in charge of the actuators 17 and the one or more medical processes $P_{MED}$ are idle. All involved processes are typically informed about and/ aware of this. In other words, the method further comprises handing over S6 ownership of control of the one or more actuators 17 from the one or more medical processes $P_{MED}$ to the remote-control process $P_{RC}$, upon at least one first pre-determined criteria being fulfilled S3. In some embodiments, the ownership of the control is handed over by performing a handshake between the one or more medical processes $P_{MED}$ and the remote-control process $P_{RC}$. The handshake assures that all processes have the same remote-control state (i.e. activated or deactivated). If remote-control is activated, it means that the remote-control process is the owner of control of the actuators 17 and vice versa.

The ownership gives a process the right to set actuator values, e.g. by writing to a defined interface. In some embodiments, the ownership of control of the one or more actuators 17 is handed over by giving the remote-control process $P_{RC}$ ownership of the writing to an interface enabling the remote-control process $P_{RC}$ to change parameters controlling the one or more actuators 17.

All processes will typically be aware of or informed about the activation of remote-control and act accordingly. In particular, the remote-control process will only act upon requests from the remote system 20 when remote-control is active.

If the protective system SS3 comprises a supervision process $P_S$, a similar procedure is performed by the supervision process $P_S$, as illustrated in FIG. 4b. Hence, if one or more second pre-determined criteria are fulfilled S41, ownership of control of the one or more auxiliary actuators 17' will be handed over from the supervision process $P_S$ to a remote-control process $P_{S-RC}$ of the protective system SS3. The one or more second pre-determined criteria assures that no ongoing therapy is jeopardised and/or that the medical device 10 will not be set in an unsafe or uncontrolled state, which would e.g. cause leakage or pressure rise. In other words, in some embodiments the one or more second pre-determined criteria comprise that that the medical procedure is idle. This is e.g. the case when the protective system P3 is inactive or idle, i.e. when no supervision is performed. In some embodiments, the second pre-determined criteria comprise that control can be handed over without risking safety (e.g. cause leakage or pressure rise) and/or that the remote system 20 is known and authorised. In other words, in some embodiments the method comprises handing over S43 ownership of control of the one or more auxiliary actuators 17' from the supervision process to a remote-control process $P_{S-RC}$ of the protective system SS3, upon second pre-determined criteria being S41 fulfilled. In some embodiments, the auxiliary actuators 17' are set S42 in a controlled state before control is handed over to the remote-control process.

Remote-control is now active. The remote-control process is then informed that it may start remotely controlling the actuators. Hence, a person outside the medical environment may now start to perform diagnosis on the medical device 10 from a remote system 20. In other words, the method comprises sending S7, by the remote-control process $P_{RC}$, an activate confirmation (i.e. a message indicating a activate confirmation), to the remote system 20 and/or to a user interface of the medical device 10. The activate confirmation is sent in response to ownership of control of the one or more actuators 17 being handed over. The activate confirmation indicates that remote-control of the one or more actuators 17 (including auxiliary actuators 17' if present) is active. The medical device 10 will then attend to remote requests to control the one or more actuators 17. Stated differently, when remote-control of the one or more actuators 17 is active, remote-control requests will be processed by the remote-control process $P_{RC}$. The activate confirmation indicates that remote-control requests will not be neglected.

If the protective system SS3 is present, the activate response is typically only sent when both the main system SS1 and the protective system SS3 have handed over ownership of control of their respective actuators 17, 17' to the respective remote-control processes. In other words, then the activate confirmation is sent in response to also the remote-control process $P_{S-RC}$ of the protective system SS3 taking over ownership of control of the one or more actuators 17 and the one or more auxiliary actuators 17' from the supervision process $P_S$.

Now turning back to FIG. 4a. Once remote-control is activated, the actuators may be remotely controlled by the remote system 20. The remote system 20 may now start to perform e.g. a support or diagnosis program. This may be done by executing a dedicated diagnosis or support software application in the remote system 20. Alternatively, a technician may input commands (e.g. actuator set values) into a user interface of the remote system 20, and in this way directly control actuators 17 of the medical device 10.

Thus, the method comprises receiving S8, from the remote system 20 by the remote-control process $P_{RC}$, control data for controlling the one or more actuators 17. In some embodiments, the control data comprises one or more actuator set values to be used by the one or more actuators. For example, the one or more actuator set values may control a temperature of a heater or a speed of a pump. In some embodiments, the control data comprises data controlling an actuator to open and/or close a valve or similar.

In some embodiments, the control data comprises data controlling an actuator to adjust rotation speed of a device in the medical device. The control data may e.g. control the rotation speed according to a certain sequence or scheme.

If it is determined S9 that remote-control is active, the actuators 17 will be controlled based on the control data. The sensors 18 may be configured to observe any related sensor value(s) that may change as an effect of the change in an actuator set value. In other words, the method further comprises controlling S10, by the remote-control process $P_{RC}$, the one or more actuators 17 based on the control data upon remote-control being active S9. Steps S8 to S10 are typically repeated for all control data for controlling the one or more actuators 17 that is received, while remote-control is active.

Remote-control will typically remain active until the remote system 20 sends a deactivate-request. Then a deactivation procedure is initiated, which will now be described with reference to FIG. 4c.

The deactivation is typically triggered by a deactivate-request (i.e. a message indicating a request to deactivate) that is sent by the remote system 20. Alternatively, the deactivate-request is received in another way e.g. via a user interface. In other words, the method further comprises receiving S11, by the remote-control process $P_{RC}$, a deactivate-request from a remote system 20. The deactivate-request requests the medical device 10 to deactivate remote-control of the one or more actuators 17.

Before remote-control is inactivated, the medical device is typically reset, such that e.g. tests or service performed by the remote system 20 will not affect a future treatment. In other words, the method further comprises setting S12, by the remote-control process $P_{RC}$, the one or more actuators 17 in a controlled state, as has been previously explained.

The method then deactivates remote-control. In other words, the method comprises handing back S13 ownership of control of one or more of the one or more actuators to the one or more medical processes. The method further comprises sending S14, from the remote-control process $P_{RC}$ to the remote system a release confirmation. The release confirmation is a message indicating that remote-control of the one or more actuators 17 has been deactivated. The release confirmation is sent in response to the ownership being handed back. All involved processes will then typically be aware of and/or informed about the deactivation. Hence, all involved processes are at each point in time aware about the remote-control state ("remote-control activated"/"remote-control inactive") and thus about who is the owner of the actuators 17 (including auxiliary actuators 17' if present).

Figure 5A:
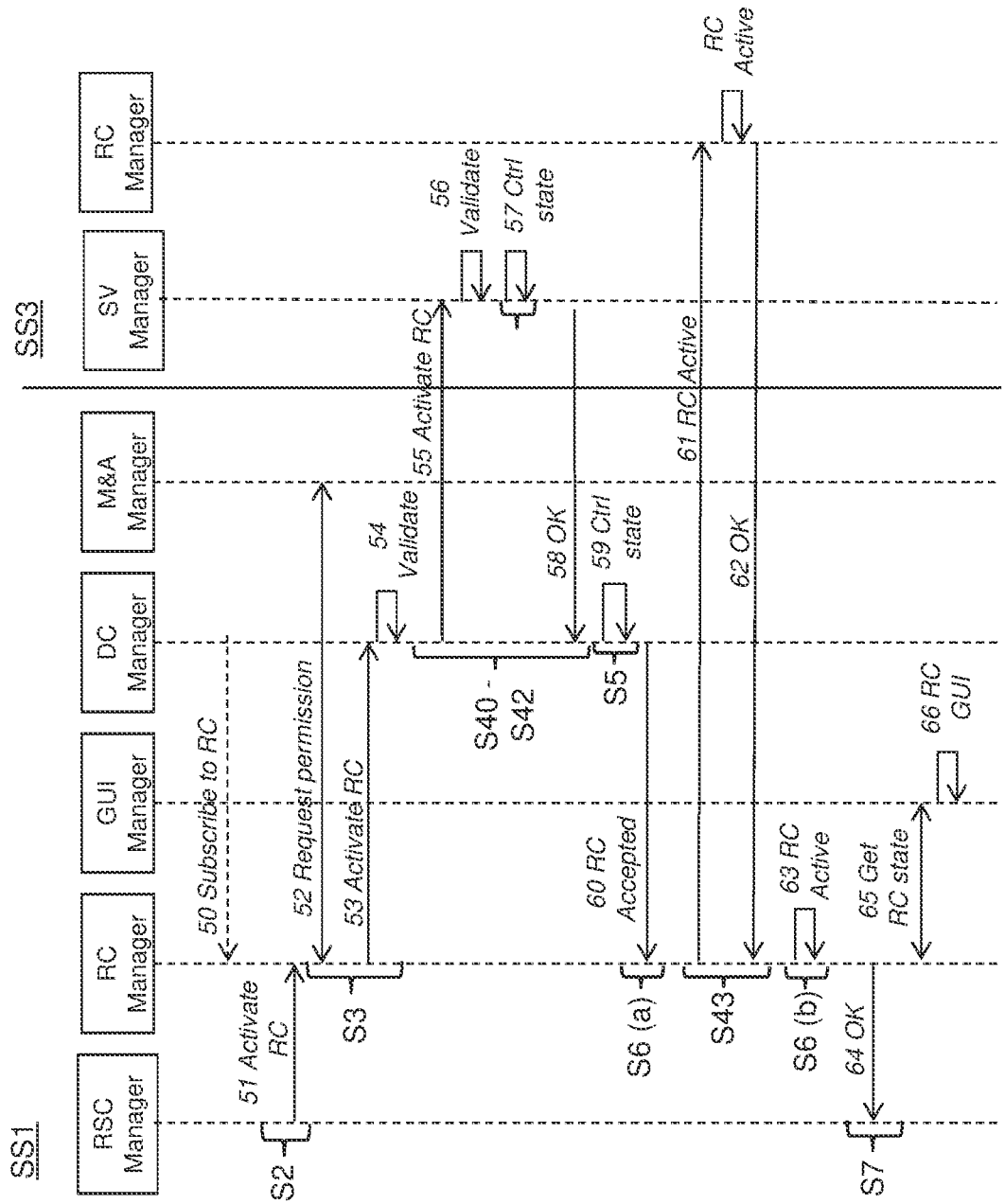
FIGS. 5a-5c are sequence diagrams of internal signalling between processes of the software system of a medical device when performing the proposed method according to one example implementation.
Figure 5B:
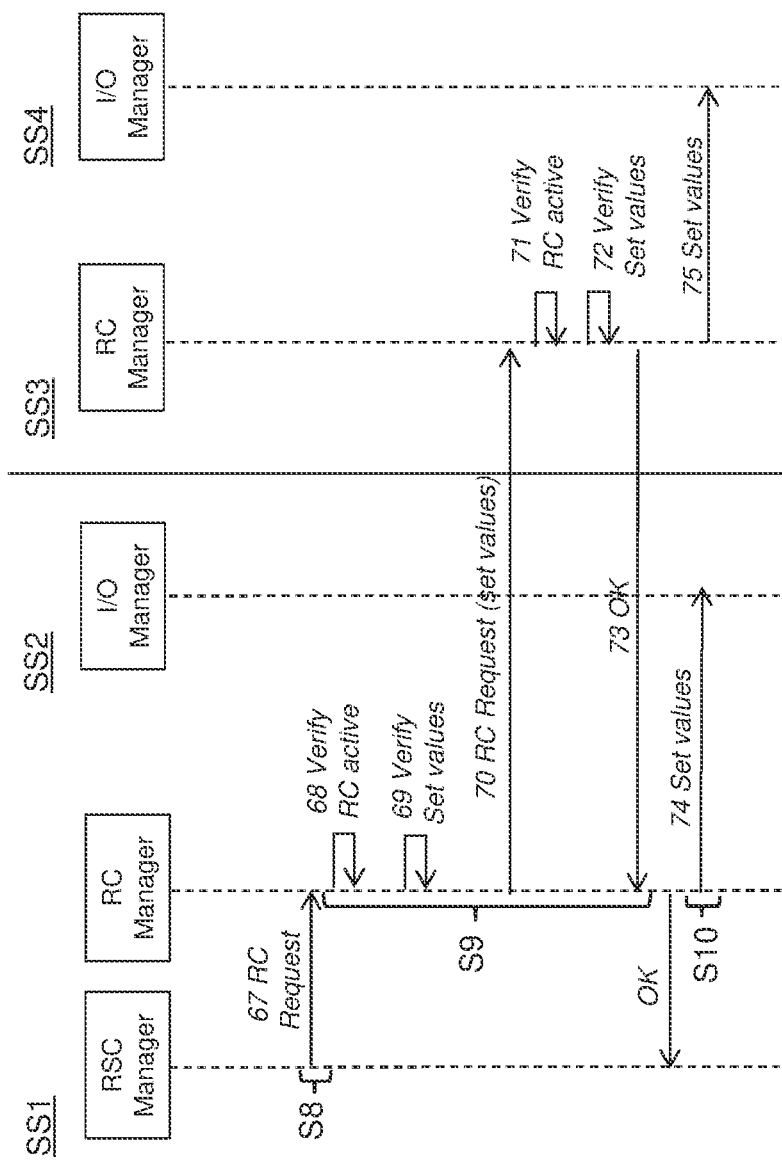
Figure 5C:
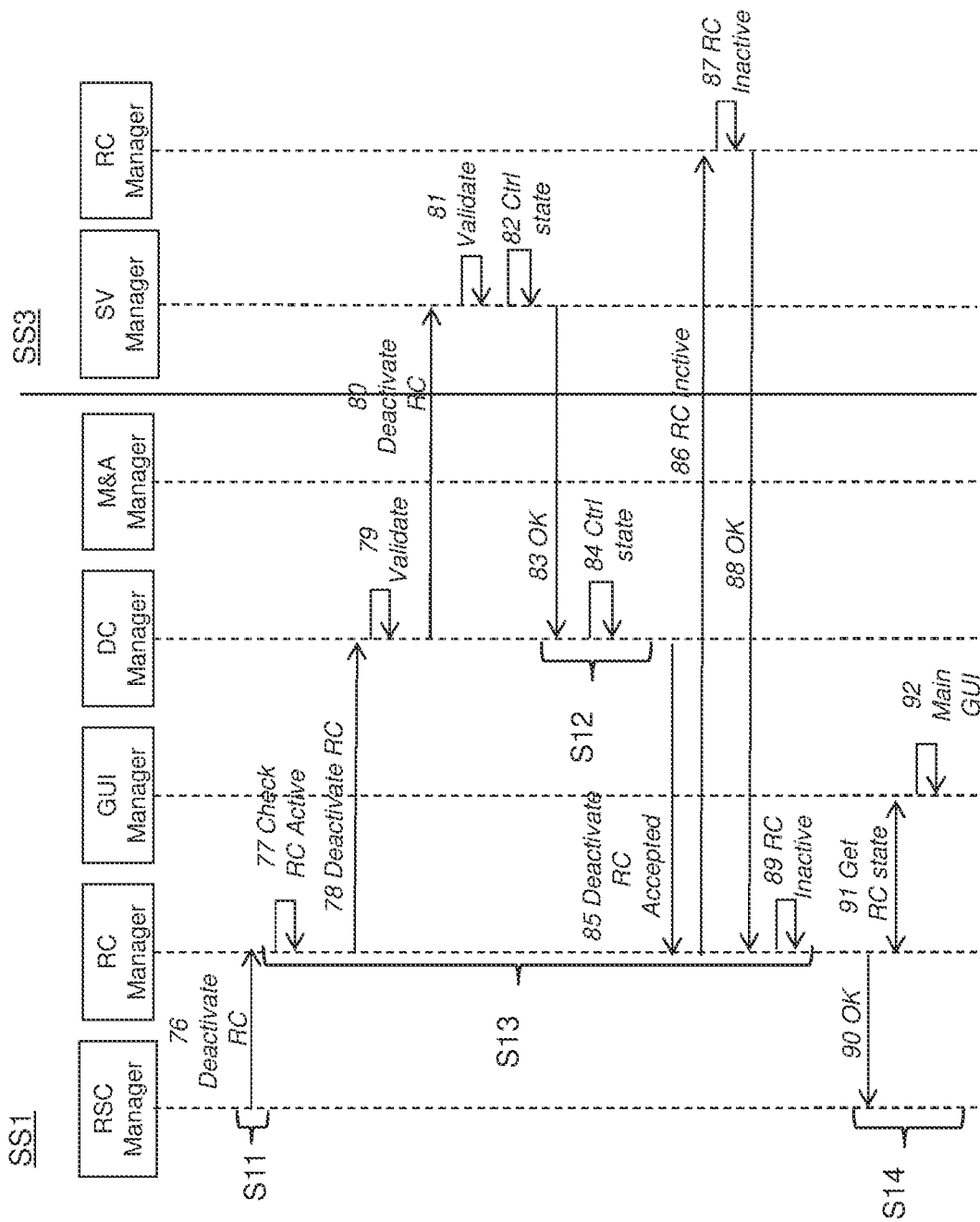

FIGS. 5a to 5c are sequence diagrams illustrating internal signalling between Software (SVV) items of an example software system of a medical device 10 when performing the proposed methods of FIGS. 4a to 4c according to an example implementation. This example implementation also refers to the medical device of FIG. 12a-1c and the example software architectures (including subsystems SS1, SS2, SS3 and SS4) described in connection with FIGS. 3a and 3b above.

The subsystems SS1, SS2, SS3 and SS4 (FIGS. 3a, 3b) are implemented by a plurality of SW items that manage different functionality of the medical device 10. A SW item is a functional part of the software architecture. A SW item can be deployed by one or several software processes. One software process may on the other hand implement one or several SW items.

However, one will often choose a one to one mapping between processes and SW items. For example, the remote-control functionality of main system SS1 and protective system SS3 is a SW item called Remote Control Manager which is typically implemented by one software process, above referred to as a remote-control process $P_{RC}$. However, it would be possible to implement this SW item as two software processes. A prerequisite though is that the processes are separate from the processes that implement the medical procedure, above referred to as medical processes ($P_{MED}$).

For simplicity, only SW items that are involved in the remote-control of the medical device 10 will be illustrated in FIGS. 5a to 5c.

The first subsystem, also referred to as main system SS1, comprises a GUI Manager, a Device Control (DC) Manager, a Mode and Access (M&A) Manager, a Remote System Communication (RSC) Manager and a Remote-control (RC) Manager. The second subsystem SS2 and fourth subsystem SS4 comprises I/O Managers. The third subsystem, or protective system SS3, comprises a Supervision (SV) Manager and a Remote-Control (RC) Manager. In this example, all processes, except RSC which is implemented by two SW items, are implemented by one corresponding SW item.

The Device Control Manager is responsible for the control of the medical device 10. The one or more medical processes $P_{MED}$ refers to all processes involved in performing the medical procedure. Hence, in this example implementation, the process implementing the Device Control Manager corresponds to a medical process $P_{MED}$ (FIG. 4a-6c).

The GUI Manager is responsible for the graphical visualization on the display 12 and for managing the user input and user output.

The Mode and Access Manager is responsible for managing the access level of the currently logged in user (or users) and the user's permissions as well as a system mode or state. The Mode and Access Manager also gives requesting SW items permission to proceed if the medical device 10 is in required system state with required user permissions. SW items can request permission to e.g. perform software update or control actuators 17 from remote.

The Supervision Manager is responsible for the supervision of the medical device during the medical procedure. The supervision process(es) $P_S$ refers to one or more processes involved in supervising the medical procedure. Hence, in this example implementation, the process implementing the Supervision Manager corresponds to a supervision process $P_S$ (FIG. 4a-c).

The I/O Manager is responsible for providing access to peripherals connected to a corresponding subsystem as described in connection to FIGS. 3a and 3b.

The Remote-Control (RC) Managers (one in main system SS1 and one in protective system SS3) are responsible for making it possible to remotely control the medical device's actuators 17 (in SS1) or auxiliary actuators 17' (in SS3). Thereby, it is possible to remotely perform e.g. diagnostic and production test sequences on the medical device 10. When remote-control is active, Device Control Manager and Supervision Manager hand over ownership of control of actuators to corresponding Remote-Control Manager (as described above and below). When remote-control is inactive the ownership is returned to Device Control Manager and Supervision Manager.

Remote System Communication (RSC) is responsible for establishing a secure (authenticated and encrypted, where applicable) connection to the remote system 20. Remote System Communication is also responsible for communicating data with the remote system. In this example implementation, Remote System Communication is divided into the following SW items:

RSC Manager: Responsible for activating the enabled functionality (retrieved from Configuration Manager) towards remote systems and converting to internal protocols.

RSC Transport: Responsible for the external protocol formatting and encryption, in general.

Remote System Communication is typically a client that is serving device internal SW items, it is not the other way around, since the medical device internal SW items are typically not dependent on the existence of Remote System Communication.

The signalling between processes in subsystems SS1 and SS3 during remote-control activation will now be described with reference to FIG. 5a.

Some prerequisites typically need to be fulfilled before the activation is initiated. For example, the remote system 20 has to be connected to the medical device 10 and the communication functionality used for "remote-control" has to be enabled. Furthermore, Device Control Manager might have to subscribe (step 50) to "activate/deactivate remote-control" notifications, in the scheme referred to as "Subscribe to RC". In addition, the cryptographic keys to be used by the secure connection needs to be installed on the medical device, e.g. at manufacturing.

There may also be some constraints on Remote-Control Manager. The Remote-Control Manager in SS1 typically supports zero to one subscriber. It is the responsibility of the subscriber to forward the activate/deactivate remote-control request as a chain and then the subscriber returns an activate/deactivate remote-control acceptance/non-acceptance to Remote-Control Manager in SS1. If no subscriber exists, Remote-Control Manager in SS1 typically accepts the activate-/deactivate-request if it has permission to proceed from Mode and Access Manager. Remote-Control Manager in SS3 does not support any subscribers but is controlled from the Remote-Control Manager in SS1.

The activation is initiated when RSC receives an "Activate remote-control (RC)" request from the remote system 20 via the communication interface 162. RSC Manager forwards (Step 51) the request to Remote-Control Manager in SS1. These steps correspond to step S2 of FIG. 4a.

The Remote-Control Manager checks (Step 52) with Mode and Access Manager that it has permission to approve the request. If it has permission to proceed, the Remote-Control Manager notifies (Step 53) Device Control Manager that an "Activate remote-control (RC)" request is received. Device Control Manager validates (Step 54) the request from a Device Control Manager perspective. These steps correspond to step S3 of FIG. 4a.

If the validation is positive, Device Control Manager then sends (Step 55) an "Activate remote-control (RC)" request to Supervision Manager, which requests that supervision should be activated. Supervision Manager validates the request (Step 56). Supervision is set into a controlled (Ctrl) state (Step 57) and sends an "OK" (Step 58) to Device Control Manager. These steps correspond to step S4-S42 of FIG. 4b.

Device Control Manager sets the actuators 17 (Step 59) in a controlled state. This step corresponds to step S5 of FIG. 4a.

Device Control Manager sends (Step 60) a remote-control acceptance (RC Accepted) to Remote-Control Manager in SS1. This steps corresponds to a first part of step S6 of FIG. 4a, here denoted S6(a).

When remote-control has been accepted, Remote-Control Manager in SS1 informs (Step 61) Remote-Control Manager in SS3 that remote-control is active (RC Active). Remote-Control Manager in SS3 updates its status to active state and returns OK (Step 62) to Remote-Control Manager in SS1. This steps corresponds to step S43 of FIG. 4b.

Remote-Control Manager in SS1 then updates (Step 63) its status to "remote-control active (RC Active)". The medical device 10 now accepts requests to control actuators from remote. This step corresponds to a second part of step S6 of FIG. 4a, here denoted S6(b).

Remote-Control Manager returns OK (Step 64) to RSC Manager, which in turn informs the remote system 20. This step corresponds to step S7 of FIG. 4a.

The GUI Manager then retrieves (Step 65) information from Remote-Control Manager that the medical device is currently in remote-control and indicates (Step 66) the information on the display 12 accordingly. For example, the display 12 will read "Remote-Control Active" and the user may then not input any commands on the display 12, i.e. the system locks the user out.

If Remote-Control Manager does not have permission to proceed (as asked in Step 52): The "activate remote-control" request is denied by Remote-Control Manager and "remote-control not permitted" is returned to the remote system 20 (via RSC Manager).

If remote-control is not approved by Device Control Manager or Supervision Manager: The "activate remote-control" request is denied by Remote-Control Manager and "activate remote-control not approved" is returned to the remote system 20 (via RSC Manager).

The signalling between processes in subsystems SS1, SS2, SS3 and SS4 while controlling actuators from the remote system 20 will now be described with reference to FIG. 5b.

Once remote-control is activated, the remote system 20 can send messages comprising one or more requests to control actuators. The requests typically comprise one or more actuator set values of the actuators to be remotely controlled. Alternatively, the one or more actuator set values are received in a subsequent message. It is possible to request one or more actuators to be set. The actuators are controlled by SS2 or SS4. RSC Manager forwards (Step 67) the one or more requests (RC Request) to Remote-Control Manager in SS1. This step corresponds to step S8 of FIG. 4a.

Remote-Control Manager verifies (Step 68) that remote-control is active and locates in which subsystem the applicable actuator(s) is/are located. Remote-Control Manager in SS1 verifies (Step 69) the actuator set value(s) for actuators 17 located in SS2 (i.e. controlled by SS2). For actuators 17 not located in SS2, Remote-Control Manager sends (Step 70) a remote-control request to Remote-Control Manager in SS3. Remote-Control Manager in SS3 verifies (Step 71) that remote-control is active and verifies (Step 72) the actuator set value(s) (e.g. verifies type and range of actuator set values) for actuators in SS4 and returns OK (Step 73) to Remote-Control Manager in SS1 before applying the actuator set value(s). When Remote-Control Manager in SS1 receives the OK response from SS3, it returns OK to RSC Manager and applies the SS2 actuator set value(s) (if any) by sending a command to SS2 (i.e. controls the actuators). These steps basically correspond to step S8 of FIG. 4a.

Remote-Control Manager in SS1 writes (Step 74) the actuator set value(s) to SS2's I/O Manager via inter system communication (ISC). I/O Manager in SS2 then acts on the actuator request(s). Remote-Control Manager in SS3 writes (Step 75) the actuator set value(s) to SS4's I/O Manager via ISC. I/O Manager in SS4 then acts on the actuator request(s). These steps correspond to step S10 of FIG. 4a.

Range and type (when defined) of the actuator set value(s) for SS1a re then verified e.g. it is verified that the actuator set value(s) has the correct range and type. For example, for each software parameter that corresponds to an actuator a specific range and type may be defined for example using metadata. For example, a pump can have an approved range of 0-90% and type=int.

If remote-control is inactive when a remote-control request is received, then the Remote-Control Manager in either SS1 or SS3 denies the request and none of them apply any actuator set value of the request. A "remote-control inactive" error message is returned to the remote system 20.

If the actuator indicated by the request is unknown, then the Remote-Control Manager in either SS1 or SS3 denies the remote-control request and none of them apply any actuator set value included in the remote-control request. An "unknown actuator" error message or signal is returned to the remote system 20.

If one or more actuator set value(s) is/are invalid (e.g. outside a predefined range of possible actuator set values of an actuator) the Remote-Control Manager in either SS1 or SS3 denies the remote-control request and none of them apply any actuator set value included in the remote-control request. An "invalid actuator set value" error message or signal is returned to the remote system.

The steps of FIG. 5*b* are repeated for every request to control actuators 17, received from the remote system 20, while remote-control is active.

The signalling between processes in subsystems SS1 and SS3 during remote-control deactivation will now be described with reference to FIG. 5*c*.

It is possible to receive a "deactivate remote-control request" from remote system 20. When receiving a "deactivate remote-control request", RSC Manager forwards (Step 76) the request to Remote-Control Manager in SS1. This step corresponds to step S11 of FIG. 4*c*.

Remote-Control Manager checks (Step 77) if remote-control is active, disapproves any future remote-control actuator set values, and notifies (Step 78) subscribers of Device Control Manager that "deactivate remote-control" request is received. Device Control Manager validates (Step 79) the request from a device control perspective and then sends (Step 80) a "deactivate remote-control" request to Supervision Manager. Supervision Manager validates (Step 81) the request and the actuators 17' are set (Step 82) into a controlled state and returns OK (Step 83) to Device Control Manager.

Device Control Managers actuators 17 are set (Step 84) into a controlled state and sends "deactivate remote-control" acceptance (i.e. an acknowledgement of the request Step 78) (Step 85) to Remote-Control Manager in SS1. When remote-control deactivation has been accepted, Remote-Control Manager in SS1 informs (Step 86) Remote-Control Manager in SS3 that remote-control is inactive. Remote-Control Manager in SS3 is now set (Step 87) in an inactive state and returns OK (Step 88) to Remote-Control Manager in SS1. Remote-Control Manager in SS1 then updates (Step 89) its status to "remote-control is not active". Remote-Control Manager returns OK (Step 90) to RSC Manager. These steps correspond to step S12 to S14 of FIG. 4*c*.

The GUI Manager then retrieves (Step 91) information from Remote-Control Manager that the medical device is currently not in remote-control and indicates (Step 92) the information on the display accordingly e.g. GUI Manager now allows user input again.

If deactivate remote-control is not approved by the Device Control or Supervision Manager: The deactivate request is denied by Remote-Control Manager in SS1 and "deactivate remote-control not approved" is returned to the remote system 20 (via RSC Manager).

The remotely controlled actuators are in an uncontrolled state when deactivating remote-control: Device Control and Supervision put all actuators in a controlled state when deactivating remote-control.

While the present invention has been described in connection with what is presently considered to be the most practical and preferred embodiments, it is to be understood that the invention is not to be limited to the disclosed embodiments, but on the contrary, is intended to cover various modifications and equivalent arrangements included within the spirit and the scope of the appended claims.

The invention claimed is:

1. A method of operating a medical device to enable a remote system to remotely control the medical device, wherein the medical device comprises a control unit having a memory and one or more actuator arranged to control a medical procedure and wherein the medical device is controlled by a software system stored in the memory, the software system including one or more medical processes involved in an operation of the medical device during the medical procedure, and a remote-control process that is separate from the one or more medical processes, wherein the remote-control process is configured to manage remote-control of the medical device from the remote system, the method comprising:
   receiving, from the remote system via the remote-control process, an activate-request requesting remote-control of the one or more actuator placing the one or more actuator is in a first controlled state;
   transferring ownership of control of the one or more actuator from the one or more medical processes to the remote-control process in response to at least one first pre-determined criteria being fulfilled, the transfer of ownership including data communication between the one or more medical processes and the remote-control process to ensure the transfer of ownership itself does not cause the one or more actuator to change from the first controlled state to a different, second controlled state; and
   sending, by the remote-control process, and in response to the ownership of control of the one or more actuator being transferred, an activate confirmation to the remote system and/or to a user interface of the medical device, the activate confirmation indicating that remote- control of the one or more actuator is active.

2. The method according to claim 1, wherein the at least one first pre-determined criteria comprises at least one of: (i) that the medical procedure is idle, (ii) that a service of the medical device is idle, (iii) that control can be handed over without risking safety, and (iv) that the remote system is known and authorized.

3. The method according to claim 1, wherein the ownership of control of the one or more actuator is, at each individual point in time when the medical device is switched on, either owned by the one or more medical processes or owned by the remote-control process.

4. The method according to claim 1, wherein the remote-control process and the one or more medical processes are separate such that they have separate memory spaces, different priorities, individual process states and/or communicate using inter process communication.

5. The method according to claim 1, comprising setting the one or more actuator in a controlled state before transferring ownership of control of the one or more actuator from the one or more medical processes to the remote-control process.

6. The method according to claim 1, comprising:
   receiving, from the remote system by the remote-control process, control data for controlling the one or more actuator; and
   controlling, by the remote-control process, the one or more actuator based on the control data upon remote-control being active.

7. The method according to claim 6, wherein the control data comprises at least one of: (i) one or more actuator set values to be used by the one or more actuator, (ii) data-used to control an actuator to open and/or close a valve, and (iii) data used to control an actuator to adjust rotation speed of a device in the medical device.

8. The method according to claim 1, comprising:
receiving, by the remote-control process, a deactivate-request from a remote system, the deactivate-request requesting the medical device to deactivate remote-control of the one or more actuator;
setting, by the remote-control process, the one or more actuator in a controlled state and transferring ownership of control of at least one of the one or more actuator from the remote-control process to the one or more medical processes, and
sending, from the remote-control process to the remote system, and in response to the ownership of control of at least one of the one or more actuator being transferred to the one or more medical processes, a release confirmation indicating that remote-control of the one or more actuator has been inactive.

9. The method according to claim 1, wherein the medical device comprises a protective system configured to supervise the medical procedure and wherein the method comprises deactivating the protective system upon the at least one first pre-determined criteria being fulfilled.

10. The method of claim 9, wherein the protective system comprises a supervision process that is separate from the one or more medical processes, wherein the supervision process is configured to control the protective system using one or more auxiliary actuators, and wherein the method comprises transferring ownership of control of the one or more auxiliary actuators from the supervision process to a remote-control process of the protective system in response to second pre-determined criteria being fulfilled, and wherein the activate confirmation is sent in response to the remote-control process of the protective system taking over ownership of control of the one or more auxiliary actuators from the supervision process.

11. The method of claim 10, wherein the second pre-determined criteria comprises: (i) that the medical procedure is idle, (ii) that the protective system is inactive or idle, (iii) that control can be handed over without risking safety, and (iv) that the remote system is known and authorized.

12. The method according to claim 1, wherein ownership of control of the one or more actuator is transferred by providing the remote-control process ownership of the writing to an interface, enabling the remote-control process to change parameters controlling the one or more actuator.

13. The method according to claim 1, wherein the one or more actuator are configured to control at least one of a valve, a pump or a heater used while performing the medical procedure.

14. The method according to claim 1, comprising providing sensor data to the remote system thereby enabling the remote system to monitor the operation of the medical device.

15. The method according to claim 1, wherein the medical device comprises at least one memory in communication with one or more processors, the one or more processors configured to perform the one or more medical processes and the remote communication process of the software system.

16. A medical device configured to perform a medical procedure, the medical device comprising:
a control unit having a memory;
one or more actuator arranged to control the medical procedure;
a communication interface configured to enable communication between the medical device and a remote system;
the memory storing a software system; and
a set of processors configured to execute the software system stored in the memory,
wherein the software system includes one or more medical processes involved in an operation of the medical device during the medical procedure, and a remote-control process that is separate from the one or more medical processes, and wherein the remote-control process is configured to manage remote-control of the medical device from the remote system, and
wherein a transfer of ownership between the one or more medical processes and the remote process includes data communication between the one or more medical processes and the remote-control process to ensure the transfer of ownership itself does not cause the one or more actuator to change from a first controlled state to a different, second controlled state.

17. The medical device of claim 16, wherein the remote-control process and the one or more medical processes are separate such that they have separate memory spaces, different priorities, individual process states and/or communicate using inter process communication.

18. The medical device of claim 16, wherein the one or more actuator is configured to control at least one of a valve, a pump or a heater used while performing the medical procedure.

19. A non-transitory, computer-readable medium storing a software system for operating a medical device to perform a medical procedure, which when executed by a processor, causes the processor to:
receive, from a remote system via a remote-control process, an activate-request requesting remote-control of one or more actuator placing the one or more actuator is in a first controlled state;
transfer ownership of control of the one or more actuator from one or more medical processes to the remote-control process, in response to at least one first pre-determined criteria being fulfilled, the transfer of ownership including data communication between the one or more medical processes and the remote-control process to ensure the transfer of ownership itself does not cause the one or more actuator to change from the first controlled state to a different, second controlled state; and
send, by the remote-control process, and in response to the ownership of control of the one or more actuator being transferred, an activate confirmation to the remote system and/or to a user interface of the medical device, the activate confirmation indicating that remote-control of the one or more actuator is active, wherein the software system includes the one or more medical processes involved in the operation of the medical device during the medical procedure, and the remote-control process that is separate from the one or more medical processes, and wherein the remote-control process is configured to manage remote-control of the medical device from the remote system.

20. The non-transitory, computer-readable medium of claim 19, wherein ownership of control of the one or more actuator is transferred by providing the remote-control process ownership of the writing to an interface, enabling the remote-control process to change parameters controlling the one or more actuator.

* * * * *